United States Patent
Kuenen

(10) Patent No.: US 12,178,556 B2
(45) Date of Patent: Dec. 31, 2024

(54) APPARATUS FOR USE WITH A WEARABLE CUFF

(71) Applicant: KONINKLIJKE PHILIPS N.V., Eindhoven (NL)

(72) Inventor: Maarten Petrus Joseph Kuenen, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 873 days.

(21) Appl. No.: 17/279,646

(22) PCT Filed: Sep. 23, 2019

(86) PCT No.: PCT/EP2019/075444
§ 371 (c)(1),
(2) Date: Mar. 25, 2021

(87) PCT Pub. No.: WO2020/064581
PCT Pub. Date: Apr. 2, 2020

(65) Prior Publication Data
US 2021/0338085 A1    Nov. 4, 2021

(30) Foreign Application Priority Data
Sep. 26, 2018 (EP) .................... 18196752

(51) Int. Cl.
*A61B 5/022*    (2006.01)
(52) U.S. Cl.
CPC ........ *A61B 5/022* (2013.01); *A61B 2503/045* (2013.01); *A61B 2503/06* (2013.01)
(58) Field of Classification Search
CPC ............ A61B 5/02208; A61B 5/02225; A61B 5/02141; A61B 5/022; A61B 2503/045; A61B 2503/06
See application file for complete search history.

(56) References Cited

U.S. PATENT DOCUMENTS 6,051,016 A * 4/2000 Mesaros ............ A61B 17/1355
                                                          606/202
6,171,254 B1 * 1/2001 Skelton .................. A61B 5/022
                                                          600/490
(Continued)

FOREIGN PATENT DOCUMENTS

EP          1958565 A1    8/2008
WO      2016030232 A1    3/2016
(Continued)

OTHER PUBLICATIONS

International Search Report and Written Opinion, International Application No. PCT/EP2019/075444, Mailed on Apr. 3, 2020.
(Continued)

*Primary Examiner* — Andrey Shostak

(57) ABSTRACT

There is provided an apparatus (12) for use with a wearable cuff (14) in measuring blood pressure. The cuff (14) is inflatable to pressurize a measurement site (20) of a subject (18). The apparatus (12) is configured to estimate a size of the cuff (14) during a current inflation of the cuff (14) and compare the estimated size of the cuff (14) to a previous size of the cuff (14) estimated during an inflation of the cuff (14) that immediately preceded the current inflation of the cuff (14). The apparatus (12) is also configured to, if the estimated size of the cuff (14) differs from the previous size of the cuff (14) by more than a predefined amount, change a pressure up to which the cuff (14) is inflated before deflation of the cuff (14) starts.

20 Claims, 2 Drawing Sheets

(56) References Cited

U.S. PATENT DOCUMENTS

| | | | |
|---|---|---|---|
| 8,808,189 B2* | 8/2014 | Tokko | A61B 5/02141 |
| | | | 600/490 |
| 2013/0046191 A1 | 2/2013 | Lin et al. | |
| 2016/0270795 A1* | 9/2016 | Krahwinkel | A61B 5/02141 |
| 2016/0331245 A1 | 11/2016 | Herndon | |
| 2018/0235488 A1* | 8/2018 | Aelen | A61B 5/02225 |

FOREIGN PATENT DOCUMENTS

| | | |
|---|---|---|
| WO | 2016055614 A1 | 4/2016 |
| WO | 2017037272 A1 | 3/2017 |
| WO | 2017129495 A1 | 8/2017 |

OTHER PUBLICATIONS

World Health Organization—Child Growth Standards, https://www.who.int/childgrowth/standards/ac_for_age/en/, Accessed Mar. 24, 2021.

Blood Pressure Levels for Boys by Age and Height Percentile, https://www.nhlbi.nih.gov/files/docs/guidelines/child_tbl.pdf, Accessed Mar. 24, 2021.

Kuo, C. et al., "Development of a Blood Pressure Measurement Instrument with Active Cuff Pressure Control Schemes", Journal of Healthcare Engineering, 2017.

Oh, H. et al., "The Modified Step-Wise Deflation Method in Blood Pressure Measurement", Computers in Cardiology 2008;35:169-172.

* cited by examiner

APPARATUS FOR USE WITH A WEARABLE CUFF

This application is the U.S. National Phase application under 35 U.S.C. § 371 of International Application No. PCT/EP2019/075444, filed on 23 Sep. 2019, which claims the benefit of European Application Serial No. 18196752.2, filed 26 Sep. 2018. These applications are hereby incorporated by reference herein.

FIELD OF THE INVENTION

The disclosure relates to an apparatus and method of operating the apparatus for use with a wearable cuff in measuring blood pressure.

BACKGROUND OF THE INVENTION

Blood pressure (BP) or, more precisely, arterial blood pressure, is the pressure exerted by circulating blood on the arterial vessel walls. It is one of the key vital signs to establish patient well-being and therefore needs to be monitored for patients at risk. Blood pressure is a periodic signal, which rises at each contraction of the heart and decreases in between heart beats. It is typically described by systolic blood pressure (SBP), diastolic blood pressure (DBP) and mean arterial blood pressure (MAP), where systolic blood pressure is the maximum blood pressure during heart cycle, diastolic blood pressure is the minimum blood pressure during heart cycle, and mean arterial blood pressure is the average blood pressure during a heart cycle.

Different techniques exist by which blood pressure can be determined and these can be classified as invasive or non-invasive measurement techniques. Typically, non-invasive measurement techniques are cuff-based, which require an inflatable cuff to be placed around a limb (which is usually the upper arm) of a subject. The pressure in the cuff is then changed to infer blood pressure. There are two common methods that use a cuff in this way, which are referred to in the art as the auscultatory method and the oscillometric method respectively.

The auscultatory method for blood pressure measurement is based on the appearance and disappearance of sounds created by the artery under the cuff during the period that the cuff pressure is changed. These sounds are referred to in the art as Korotkoff sounds. The pressures at which the Korotkoff sounds appear and vanish are indicative of DBP and SBP with Korotkoff sounds appearing at each heart beat between DBP and SBP. The measurement of sound can be performed manually with a stethoscope that is placed over the artery just below the cuff, or in an automated way with a microphone under the cuff.

In the oscillometric method for blood pressure measurement, the systolic and diastolic blood pressure values are based on small volume oscillations or pressure oscillations that are induced in the cuff by each heart beat. The amplitude of these volume or pressure oscillations depends on the difference between the cuff pressure and the actual arterial blood pressure. Systolic blood pressure and diastolic blood pressure are then determined as the cuff pressure where the volume or pressure oscillations have amplitudes of a certain fraction of the maximum oscillation amplitude. These fractions are typically heuristically determined.

In both the auscultatory and oscillometric method, the mean arterial pressure is typically calculated as: $MAP = \frac{2}{3} \cdot DBP + \frac{1}{3} \cdot SBP$.

The oscillometric and auscultatory measurement methods can be performed either during inflation of the cuff or during deflation of the cuff. Conventionally, measurements during deflation are used, in which the cuff is rapidly inflated to a level above the SBP where the blood flow in the artery under the cuff is blocked, after which cuff pressure is decreased gradually or in a stepwise manner. During deflation, the volume or pressure oscillations or the Korotkoff sounds are measured. While deflation stage measurement is well-established, an issue exists in the discomfort it introduces to the subject. In particular, the subject is exposed to a relatively high cuff pressure for a certain amount of time and pressures above a certain level can be uncomfortable and even painful, either due to the pressure exerted by the cuff itself or due to a build-up of venous blood in the clamped extremity (namely, venous pooling). The longer these pressures are applied to the subject, the higher the discomfort level is for the subject.

Another issue with utilizing the deflation based blood pressure measurement is that the process of inflating the cuff and then deflating the cuff can be considerably long, where each measurement during deflation typically takes 40 seconds to complete. Also, since a defined maximum pressure level needs to be achieved before the deflation procedure can be initiated, the subject is exposed to a maximum cuff pressure that is higher than that required for the blood pressure measurement itself. Furthermore, the inherent variability of blood pressure over time can distort a single blood pressure measurement.

These issues may be worsened if the blood pressure measurement is not started at an appropriately selected pressure. If the starting pressure is too low, this can cause a blood pressure measurement to take longer than necessary, since the issue needs to be detected and subsequently the pump has to further inflate the cuff. Similarly, if the starting pressure is too high, this can also causes a blood pressure measurement to take longer and an excessively high pressure level can add to the discomfort experienced by the subject. For example, a blood pressure measurement for a hypertensive adult may lead to starting pressures that are beyond 200 mmHg, which can cause excessive discomfort to a younger subject for which a blood pressure measurement is subsequently acquired. For example, an excessively high starting pressure can be especially problematic in pediatric subjects (e.g. infants, such as a neonates, children, or adolescents).

A starting pressure for a blood pressure measurement may be determined based on past blood pressure measurements and, in particular, based on a previously measured systolic blood pressure value. However, this technique for determining a starting pressure for a blood pressure measurement only works well if the same subject is being measured; it does not lead to an appropriate starting pressure whenever the subject has changed since the last blood pressure measurement.

SUMMARY OF THE INVENTION

As noted above, a limitation associated with existing techniques for measuring blood pressure is that it is not currently possible to start a blood pressure measurement for a subject at a pressure that is appropriate for the subject, when the subject has changed since the last blood pressure measurement. Also, starting a blood pressure measurement at a pressure that is not appropriate for the subject can cause a variety of issues. It would thus be valuable to address the limitation associated with existing techniques.

Therefore, according to a first aspect, there is provided an apparatus for use with a wearable cuff in measuring blood pressure. The cuff is inflatable to pressurize a measurement site of a subject. The apparatus is configured to estimate a size of the cuff during a current inflation of the cuff and compare the estimated size of the cuff to a previous size of the cuff estimated during an inflation of the cuff that immediately preceded the current inflation of the cuff. The apparatus is also configured to, if the estimated size of the cuff differs from the previous size of the cuff by more than a predefined amount, change a pressure up to which the cuff is inflated before deflation of the cuff starts.

In some embodiments, the apparatus may be configured to change the pressure up to which the cuff is inflated before deflation of the cuff starts based on the estimated size of the cuff. In some embodiments, the apparatus may be configured to change the pressure up to which the cuff is inflated before deflation of the cuff starts based on the estimated size of the cuff by being configured to determine an expected blood pressure range for the subject based on the estimated size of the cuff and change the pressure up to which the cuff is inflated before deflation of the cuff starts based on the determined expected blood pressure range for the subject.

In some embodiments, the apparatus may be configured to determine the expected blood pressure range for the subject based on the estimated size of the cuff by being configured to compare the estimated size of the cuff to a plurality of reference sizes of the cuff, each stored with a corresponding reference blood pressure range, and determine the expected blood pressure range for the subject as the reference blood pressure range that is stored with the reference size of the cuff that is the same as or differs the least from the estimated size of the cuff. In some embodiments, the plurality of reference sizes of the cuff and corresponding reference blood pressure ranges may be based on data acquired from a population.

In some embodiments, the apparatus may be configured to, if the estimated size of the cuff differs from the previous size of the cuff by less than the predefined amount or if the estimated size of the cuff is the same as the previous size of the cuff, determine the pressure up to which the cuff is inflated before deflation of the cuff starts based on a blood pressure value determined during a deflation of the cuff that immediately preceded the current inflation of the cuff.

In some embodiments, the apparatus may be configured to estimate the size of the cuff during the current inflation of the cuff based on a time taken for the cuff to be inflated from a baseline pressure up to a predefined pressure. In some embodiments, the apparatus may be configured to estimate the size of the cuff during the current inflation of the cuff based on an average speed at which the cuff inflates. In some embodiments, the apparatus may be configured to determine the average speed at which the cuff inflates as the average speed at which the cuff inflates once a predefined time period after a start of the current inflation of the cuff has passed.

In some embodiments, the apparatus may be configured to estimate the size of the cuff during the current inflation of the cuff based on an internal volume of the cuff. In some embodiments, the apparatus may be configured to estimate the size of the cuff during the current inflation of the cuff based on a volume of fluid into the cuff and a maximum pressure up to which the cuff is inflated. In some embodiments, the apparatus may be configured to estimate the size of the cuff during the current inflation of the cuff based on a measure of a compliance of the cuff.

According to a second aspect, there is provided a system for use in measuring blood pressure. The system comprises the apparatus as described above and the wearable cuff that is inflatable to pressurize the measurement site of the subject.

According to a third aspect, there is provided a method of operating an apparatus for use with a wearable cuff in measuring blood pressure. The cuff is inflatable to pressurize a measurement site of a subject. The method comprises estimating a size of the cuff during a current inflation of the cuff and comparing the estimated size of the cuff to a previous size of the cuff estimated during an inflation of the cuff that immediately preceded the current inflation of the cuff. The method also comprises, if the estimated size of the cuff differs from the previous size of the cuff by more than a predefined amount, changing a pressure up to which the cuff is inflated before deflation of the cuff.

According to a fourth aspect, there is provided a computer program product comprising a computer readable medium, the computer readable medium having computer readable code embodied therein, the computer readable code being configured such that, on execution by a suitable computer or processor, the computer or processor is caused to perform the method described above.

According to the aspects and embodiments described above, the limitations of existing techniques are addressed. In particular, the above-described aspects and embodiments ensure that a pressure up to which a cuff is inflated before deflation of the cuff starts is changed where a size of the cuff estimated during a current inflation of the cuff differs from a previous size of the cuff by more than a predefined amount. In this way, it can be ensured that the pressure at which deflation of the cuff is started is a more appropriate pressure for the particular subject for which a blood pressure measurement is to be acquired, even when the subject has changed since the last blood pressure measurement. In effect, the pressure at which deflation of the cuff is started can be optimized for the particular subject for which a blood pressure measurement is to be acquired. As the pressure at which deflation of the cuff is started is more appropriate for the subject, it is possible to reduce the discomfort experienced by the subject and/or to increase the speed at which blood pressure measurements can be acquired for the subject.

The limitations associated with the existing techniques discussed earlier are therefore addressed by way of the above-described aspects and embodiments.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

Figure 1:
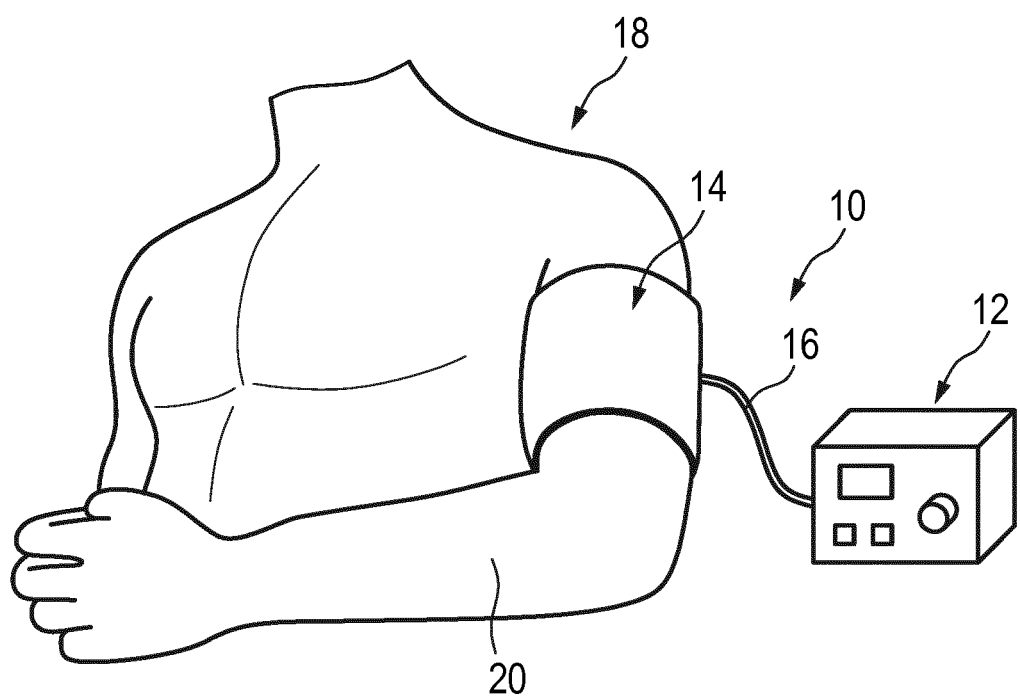
FIG. 1 is a simplified schematic illustration of an apparatus in use with a wearable cuff according to an example embodiment.

There is provided herein an apparatus for use with a wearable cuff (or clamp unit) in measuring blood pressure, which overcomes the limitations with existing techniques. The wearable cuff referred to herein is inflatable to pressurize a measurement site of a subject (e.g. a patient). In this way, the wearable cuff can pressurize an artery in the measurement site of the subject. Typically, the wearable cuff can be supplied with a fluid (e.g. a gas, such as air, or any other fluid) suitable for inflating the wearable cuff. The wearable cuff can be inflatable to pressurize the measurement site of a subject (and thus an artery in the measurement site of the subject) at the pressure of the fluid in the wearable cuff.

The wearable cuff is configured to be worn on or around (e.g. wrapped around, attached to, or fastened to) the measurement site of the subject. The measurement site of the subject can be any site on the body of the subject that is suitable for use in measuring a blood pressure of the subject, such as any site on the body of the subject that comprises an artery. For example, the measurement site of the subject may be located on a limb of the subject, such as an arm (e.g. an upper arm or a forearm) of the subject. Thus, the wearable cuff can be configured to be worn on or around (e.g. wrapped around, attached to, or fastened to) a limb of the subject. The subject referred to herein can be, for example, an adult or a pediatric subject, e.g. an infant, a child or an adolescent. An infant can, for example, be a neonate, such as a pre-term or premature infant, a full-term infant or a post-term infant.

Briefly, the apparatus described herein is configured to estimate a size of the cuff (or cuff size) during a current inflation of the cuff and compare the estimated size of the cuff to a previous size of the cuff estimated during an inflation of the cuff that immediately preceded the current inflation of the cuff 14. The apparatus is also configured to, if the estimated size of the cuff differs from the previous size of the cuff by more than a predefined amount, change a pressure up to which the cuff is inflated before deflation of the cuff starts. The pressure up to which the cuff is inflated before deflation of the cuff starts may also be referred to as "the starting pressure", "the starting pressure for deflation", or, more specifically, "the starting pressure for a blood pressure measurement".

The apparatus described herein can be implemented in numerous ways, with software and/or hardware, to perform the various functions described herein. In particular implementations, the apparatus can comprise a plurality of software and/or hardware modules, each configured to perform, or that are for performing, individual or multiple steps of the method described herein. The apparatus may comprise one or more processors (such as one or more microprocessors, one or more multi-core processors and/or one or more digital signal processors (DSPs)), one or more processing units, and/or one or more controllers (such as one or more microcontrollers) that may be configured or programmed (e.g. using software or computer program code) to perform the various functions described herein. The apparatus may be implemented as a combination of dedicated hardware (e.g. amplifiers, pre-amplifiers, analog-to-digital convertors (ADCs) and/or digital-to-analog convertors (DACs)) to perform some functions and a processor (e.g. one or more programmed microprocessors, DSPs and associated circuitry) to perform other functions.

FIG. 1 illustrates the apparatus 12 in use with a wearable cuff 14 in measuring blood pressure, according to an example embodiment. There is thus provided a system 10 comprising the apparatus 12 and the cuff 14. As mentioned earlier, the cuff 14 is inflatable to pressurize the measurement site 20 of the subject 18. In the example embodiment illustrated in FIG. 1, the measurement site 20 of the subject 18 is located on the arm or, more specifically, the upper arm of the subject 18. Thus, the cuff 14 is worn on or around (e.g. wrapped around, attached to, or fastened to) the upper arm of the subject 18 in this illustrated example embodiment.

As mentioned earlier, the apparatus 12 is configured to estimate a size of the cuff 14 during a current inflation of the cuff 14 and compare the estimated size of the cuff 14 to a previous size of the cuff 14 estimated during an inflation of the cuff 14 that immediately preceded the current inflation of the cuff 14. The apparatus 12 is also configured to, if the estimated size of the cuff 14 differs from the previous size of the cuff 14 by more than a predefined amount, change a pressure up to which the cuff 14 is inflated before deflation of the cuff 14 starts.

As illustrated in FIG. 1, in some embodiments, the cuff 14 may be coupled with or connected to the apparatus 12 via at least one supply line (or at least one supply tube) 16, which may also be referred to as at least one pressure supply line (or at least one pressure supply tube) 16. The at least one supply line 16 can be arranged for pressurizing the cuff 14 and, consequently, the measurement site 20 of the subject 18. The at least one supply line 16 may be provided for inflating and/or deflating the cuff 14. As an alternative to the at least one supply line 16, in other embodiments (not illustrated), the apparatus 12 can be coupled directly to (e.g. mounted directly on) the cuff 14. As mentioned earlier, the cuff 14 can be supplied with any fluid suitable for inflating the cuff 14.

Although not illustrated in FIG. 1, in some embodiments, the system 10 may comprise a pump. The pump can be controllable to inflate the cuff 14 in the manner described herein. In some embodiments, the apparatus 12 described herein may comprise the pump. Alternatively or in addition, a pump may be external to (e.g. separate to or remote from) the apparatus 12. A pump can thus be any pump that is controllable to inflate the cuff 14. In some embodiments, the pump can be controllable by the apparatus 12 or, more specifically, a controller (not illustrated in FIG. 1) of the apparatus 12 to inflate the cuff 14 in the manner described herein. The apparatus 12 (or the controller of the apparatus 12) may communicate with and/or connect to the pump in any suitable way to control the pump.

Although also not illustrated in FIG. 1, in some embodiments, the system 10 may comprise a deflation valve. The deflation valve can be controllable to deflate the cuff 14. In some embodiments, the apparatus 12 described herein may comprise the deflation valve. Alternatively or in addition, a deflation valve may be external to (e.g. separate to or remote from) the apparatus 12. A deflation valve can thus be any valve that is controllable to deflate the cuff 14. In some embodiments, the deflation valve can be controllable by the apparatus 12 or, more specifically, a controller (not illustrated in FIG. 1) of the apparatus 12 to deflate the cuff 14. The apparatus 12 (or the controller of the apparatus 12) may communicate with and/or connect to the deflation valve in any suitable way to control the deflation valve.

Although also not illustrated in FIG. 1, in some embodiments, the system 10 may comprise at least one pressure sensor. The at least one pressure sensor can be configured to measure the pressure in the cuff 14. In some embodiments, the apparatus 12 described herein may comprise the at least one pressure sensor configured to measure the pressure in the cuff 14. Alternatively or in addition, at least one pressure sensor external to (e.g. separate to or remote from) the apparatus 12 may be configured to measure the pressure in the cuff 14. For example, in some embodiments, the cuff 14 itself may comprise at least one pressure sensor configured to measure the pressure in the cuff 14. In some embodiments, the at least one pressure sensor can be controllable by the apparatus 12 or, more specifically, a controller (not illustrated in FIG. 1) of the apparatus 12 to measure the pressure in the cuff 14. The apparatus 12 (or the controller of the apparatus 12) may communicate with and/or connect to the at least one pressure sensor in any suitable way to control the at least one pressure sensor.

Although also not illustrated in FIG. 1, in some embodiments, the system 10 may comprise a communications interface (or communications circuitry). In some embodiments, the apparatus 12 described herein may comprise a communications interface. Alternatively or in addition, the communications interface may be external to (e.g. separate to or remote from) the apparatus 12. The communications interface can be for enabling the apparatus 12, or components of the apparatus 12, to communicate with and/or connect to one or more other components, sensors, interfaces, devices, or memories (such as any of those described herein). For example, the communications interface can be for enabling the apparatus 12 (or the controller of the apparatus 12) to communicate with and/or connect to any one or more of the pump, the deflation valve, and the at least one pressure sensor described earlier. The communications interface may enable the apparatus 12, or components of the apparatus 12, to communicate and/or connect in any suitable way. For example, the communications interface may enable the apparatus 12, or components of the apparatus 12, to communicate and/or connect wirelessly, via a wired connection, or via any other communication (or data transfer) mechanism. In some wireless embodiments, for example, the communications interface may enable the apparatus 12, or components of the apparatus 12, to use radio frequency (RF), Bluetooth, or any other wireless communication technology to communicate and/or connect.

Although also not illustrated in FIG. 1, in some embodiments, the system 10 may comprise a memory. In some embodiments, the apparatus 12 described herein may comprise the memory. Alternatively or in addition, the memory may be external to (e.g. separate to or remote from) the apparatus 12. The apparatus 12 (or the controller of the apparatus 12) may be configured to communicate with and/or connect to the memory. The memory may comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM), and electrically erasable PROM (EEPROM). In some embodiments, the memory can be configured to store program code that can be executed by a processor to cause the apparatus 12 to operate in the manner described herein.

Alternatively or in addition, in some embodiments, the memory can be configured to store information required by or resulting from the method described herein. For example, in some embodiments, the memory may be configured to store any one or more of the estimated size of the cuff 14, the previous size of the cuff 14, the changed pressure up to which the cuff 14 is inflated before deflation of the cuff 14 starts, one or more blood pressure values determined for the subject during use of the apparatus 12 described herein, or any other information, or any combination of information, required by or resulting from the method described herein. In some embodiments, the apparatus 12 (or the controller of the apparatus 12) can be configured to control the memory to store information required by or resulting from the method described herein.

Although also not illustrated in FIG. 1, the system 10 may comprise a user interface. In some embodiments, the apparatus 12 described herein may comprise the user interface. Alternatively or in addition, the user interface may be external to (e.g. separate to or remote from) the apparatus 12. The apparatus 12 (or the controller of the apparatus 12) may be configured to communicate with and/or connect to a user interface. The user interface can be configured to render (or output, display, or provide) information required by or resulting from the method described herein. For example, in some embodiments, the user interface may be configured to render (or output, display, or provide) one or more of the estimated size of the cuff 14, the previous size of the cuff 14, the changed pressure up to which the cuff 14 is inflated before deflation of the cuff 14 starts, one or more blood pressure values determined for the subject during use of the apparatus 12 described herein, or any other information, or any combination of information, required by or resulting from the method described herein. Alternatively or in addition, the user interface can be configured to receive a user input. For example, the user interface may allow a user to manually enter information or instructions, interact with and/or control the apparatus 12. Thus, the user interface may be any user interface that enables the rendering (or outputting, displaying, or providing) of information and, alternatively or in addition, enables a user to provide a user input. In some embodiments, the apparatus 12 (or the controller of the apparatus 12) can be configured to control the user interface to operate in the manner described herein.

For example, the user interface may comprise one or more switches, one or more buttons, a keypad, a keyboard, a mouse, a touch screen or an application (for example, on a smart device such as a tablet, a smartphone, or any other smart device), a display or display screen, a graphical user interface (GUI) such as a touch screen, or any other visual component, one or more speakers, one or more microphones or any other audio component, one or more lights (such as light emitting diode LED lights), a component for providing tactile or haptic feedback (such as a vibration function, or any other tactile feedback component), an augmented reality device (such as augmented reality glasses, or any other augmented reality device), a smart device (such as a smart mirror, a tablet, a smart phone, a smart watch, or any other smart device), or any other user interface, or combination of user interfaces. In some embodiments, the user interface that is controlled to render information may be the same user interface as that which enables the user to provide a user input.

Although also not illustrated in FIG. 1, the apparatus 12 may comprise a battery or other power supply for powering the apparatus 12 or means for connecting the apparatus 12 to a mains power supply. It will also be understood that the apparatus 12 may comprise any other component to those described herein or any combination of components.

Figure 2:
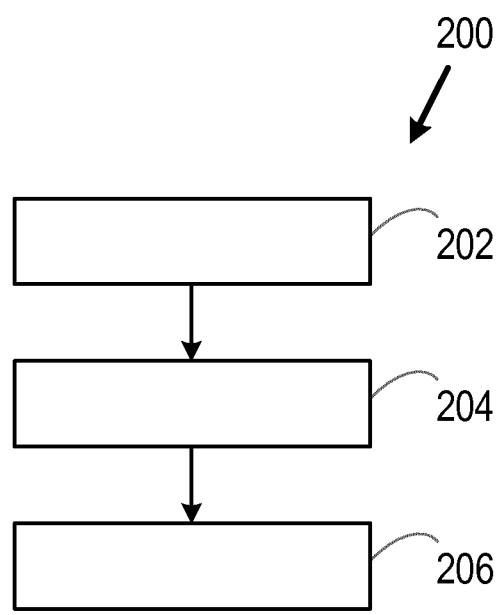
FIG. 2 is a flow chart illustrating a method of operating the apparatus according to an embodiment.

FIG. 2 illustrates a method 200 of operating the apparatus 12 described herein for use with a wearable cuff 14 in measuring blood pressure according to an embodiment. As mentioned earlier, the cuff 14 is inflatable to pressurize a measurement site 20 of a subject 18. The method 200 can generally be performed by or under the control of the apparatus 12 (or the controller of the apparatus 12) described earlier. At block 202 of FIG. 2, a size of the cuff 14 (or cuff size) is estimated during a current inflation of the cuff 14. The inflation of the cuff 14 is where the cuff 14 is inflated from a baseline pressure $p_{base}$ up to a predefined pressure $p_1$.

In some embodiments, the baseline pressure $p_{base}$ can be a pressure in a range from 0 to 30 mmHg, for example a pressure in a range from 5 to 25 mmHg, for example a pressure in a range from 10 to 20 mmHg. For example, the baseline pressure $p_{base}$ may be a pressure selected from 0 mmHg, 5 mmHg, 10 mmHg, 15 mmHg, 20 mmHg, 25 mmHg, 30 mmHg, or any integer or non-integer value between these example pressures.

In some embodiments, the predefined pressure $p_1$ can be the immediately preceding starting pressure for deflation. The immediately preceding starting pressure for deflation is the pressure up to which the cuff 14 was inflated during the inflation that immediately preceded the current inflation. In other embodiments, the predefined pressure $p_1$ can be an arbitrary pressure that is greater than the baseline pressure $p_{base}$. For example, the predefined pressure $p_1$ can be an arbitrary pressure that is less than the immediately preceding starting pressure for deflation but greater than the baseline pressure $p_{base}$.

In some embodiments, the predefined pressure $p_1$ may be a pressure in a range from 60 to 100 mmHg, for example a pressure in a range from 65 to 95 mmHg, for example a pressure in a range from 70 to 90 mmHg, for example a pressure in a range from 75 to 85 mmHg. For example, the predefined pressure $p_1$ may be a pressure selected from 60 mmHg, 65 mmHg, 70 mmHg, 75 mmHg, 80 mmHg, 85 mmHg, 90 mmHg, 95 mmHg, 100 mmHg, or any integer or non-integer value between these example pressures. In some embodiments, the predefined pressure $p_1$ may be a pressure of at least 60 mmHg, for example at least 65 mmHg, for example at least 70 mmHg, for example at least 75 mmHg, for example at least 80 mmHg, for example at least 85 mmHg, for example at least 90 mmHg, for example at least 95 mmHg, for example at least 100 mmHg.

The apparatus 12 can be configured to estimate the size of the cuff 14 during the current inflation of the cuff 14 in any suitable way. In some embodiments, the apparatus 12 can be configured to estimate the size of the cuff 14 during the current inflation of the cuff 14 based on one or more characteristics of the cuff 14. In some embodiments, for example, the apparatus 12 can be configured to estimate the size of the cuff 14 during the current inflation of the cuff 14 based on a pressure in the cuff 14 and optionally also pump flow.

For example, in some embodiments, the apparatus 12 may be configured to estimate the size of the cuff 14 during the current inflation of the cuff 14 based on a time taken for the cuff 14 to be inflated from the baseline pressure $p_{base}$ described earlier up to the predefined pressure $p_1$ described earlier.

Alternatively or in addition, in some embodiments, the apparatus 12 may be configured to estimate the size of the cuff 14 during the current inflation of the cuff 14 based on a speed (e.g. an average speed) at which the cuff 14 inflates. In some of these embodiments, it may be assumed that the pump flow is always the same. In some embodiments, the apparatus 12 may be configured to determine the speed at which the cuff 14 inflates as the speed (e.g. the average speed) at which the cuff 14 inflates once a predefined time period after a start of the current inflation of the cuff 14 has passed. Thus, according to some embodiments, a predefined time period after the start of the current inflation of the cuff 14 may be omitted or excluded from the determination of the speed (e.g. the average speed) at which the cuff 14 inflates. In this way, the determination can be made less sensitive to resistance from components of the system 10, such as from the at least one supply line (or at least one supply tube) 16.

In some embodiments, the apparatus 12 may be configured to determine the speed (e.g. the average speed) at which the cuff 14 inflates by dividing an increase in pressure in the cuff 14 measured during the current inflation of the cuff 14 by the time taken for the increase in pressure in the cuff 14. Here, the increase in pressure in the cuff 14 is the increase in pressure in the cuff 14 from the baseline pressure $p_{base}$ described earlier up to the predefined pressure $p_1$ described earlier. That is, in some embodiments, the apparatus 12 may be configured to determine the speed (e.g. the average speed) s(t) at which the cuff 14 inflates using the following equation:

$$s(t) = \frac{p(t) - p(t_0)}{t - t_0}, \qquad (1)$$

where $p(t)-p(t_0)$ is the change in pressure in the cuff 14 over time from a starting time $t_0$ to the time t at which the increase in pressure in the cuff 14 is measured and $t-t_0$ is the time taken for the increase in pressure in the cuff 14 or, more specifically, the time from the starting time $t_0$ to the time t at which the increase in pressure in the cuff 14 is measured. In some embodiments, the starting time $t_0$ may be a time at which the pressure in the cuff 14 first exceeds the baseline pressure $p_{base}$ described earlier. Similarly, in some embodiments, the time t at which the increase in pressure in the cuff 14 is measured may be the time at which the pressure in the cuff 14 reaches the predefined pressure $p_1$ described earlier. In this way, the determination of the speed (e.g. the average speed) at which the cuff 14 inflates can be made less sensitive to differences in cuff wrapping.

In some embodiments, the apparatus 12 can be configured to determine the speed (e.g. the average speed) at which the cuff 14 inflates at various pressure levels during the current inflation of the cuff 14, e.g. at various pressure levels in a range from the baseline pressure $p_{base}$ described earlier to the predefined pressure $p_1$ described earlier. In some of these embodiments, the apparatus 12 can be configured to store the determined speed (e.g. the average speed) at which the cuff 14 inflates at the various pressure levels. For example, the apparatus 12 can be configured to control the memory described earlier to store the determined speed (e.g. the average speed) at which the cuff 14 inflates at the various pressure levels in some of these embodiments.

In some embodiments, the apparatus 12 may be configured to acquire, from the at least one pressure sensor mentioned earlier, the measured increase in pressure in the cuff 14 and optionally also the time taken for the measured increase. In some embodiments, the speed (e.g. the average speed) at which the cuff 14 inflates may be determined in real-time. The speed (e.g. the average speed) at which the cuff 14 inflates can be indicative of the size of the cuff 14 according to some embodiments. For example, a smaller cuff is inflated faster than a larger cuff. Thus, the slower the speed (e.g. the average speed) at which the cuff 14 inflates, the smaller the cuff 14. Similarly, the faster the speed (e.g. the average speed) at which the cuff 14 inflates, the larger the cuff 14.

Alternatively or in addition, in some embodiments, the apparatus 12 may be configured to estimate the size of the cuff 14 during the current inflation of the cuff 14 based on an internal volume of the cuff 14. In some embodiments, the internal volume of the cuff 14 may be determined by acquiring a measure of a flow of fluid realized by a pump that is controllable to inflate the cuff 14 (such as the pump mentioned earlier) and integrating the measure of the flow of fluid realized by the pump over time. In some embodiments, the measure of the flow of fluid realized by the pump may be acquired from a memory (such as that mentioned earlier), e.g. from a look-up table stored in the memory. For example, the memory may store measures of a flow of fluid realized by the pump as a function of a pressure in the cuff 14 that can be achieved by the pump (e.g. in the form of a look-up table). Thus, in some embodiments, the pressure in the cuff 14 can be measured and used to acquire the flow of fluid stored in the memory for the measured pressure.

In some embodiments, the measure of the flow of fluid realized by the pump may be acquired based on a measurement of a rotation speed of the pump. For example, in the case of a diaphragm pump, each rotation of the pump results in the emptying of a fixed number of pump chambers. Each pump chamber has a fixed volume and thus the fluid volume that can theoretically be displaced in a single rotation of the pump can be determined. The efficiency of the pump can be measured and used to determine the measure of the flow of fluid realized by the pump. For example, the measure of the flow of fluid realized by the pump may be determined as the rotation speed of the pump multiplied by the efficiency of the pump. Alternatively, the measure of the flow of fluid realized by the pump may be acquired from a memory (such as that mentioned earlier), e.g. from a look-up table stored in the memory. For example, the memory may store measures of a flow of fluid realized by the pump as a function of the rotation speed of the pump and the pressure in the cuff 14. Thus, in some embodiments, the pressure in the cuff 14 can be measured and used with the rotation speed of the pump to acquire the flow of fluid stored in the memory for the measured pressure and rotation speed.

Alternatively or in addition, in some embodiments the apparatus 12 may be configured to estimate the size of the cuff 14 during the current inflation of the cuff 14 based on a volume (or flow) of fluid into the cuff 14 and a maximum pressure up to which the cuff 14 is inflated (e.g. a maximum pressure that can be achieved in the cuff 14). A person skilled in the art will be aware of ways in which to estimate the size of the cuff 14 based on the volume (or flow) of fluid into the cuff 14 and the maximum pressure up to which the cuff 14 is inflated.

Alternatively or in addition, in some embodiments, the apparatus 12 may be configured to estimate the size of the cuff 14 during the current inflation of the cuff 14 based on a measure of a compliance of the cuff 14. The compliance of the cuff 14 may also be referred to in the art as the "cuff compliance" for the cuff 14. The cuff compliance can be defined as a value that relates a pressure change in the cuff 14 due to a volume change of the cuff 14.

In some embodiments, the cuff compliance $C_c$ may be determined from the following equation:

$$C_c(P_c) = \frac{dV_c}{dP_c}, \tag{2}$$

where $V_c$ is the volume of the cuff 14 and $P_c$ is the pressure in the cuff 14. In first order, the cuff compliance $C_c$ can be determined using Boyle's Law. The cuff compliance $C_c$ varies depending on the pressure in the cuff 14. In some embodiments, the cuff compliance may be determined as an inflation flow into the cuff 14 (i.e. a flow of fluid into the cuff 14 to inflate the cuff 14) divided by an inflation rate of the cuff 14 (i.e. the rate at which the cuff 14 inflates).

In some embodiments, a quasi-static cuff compliance $C_{QS}$ may be determined using the following procedure. The pressure in the cuff 14 over time dP/dt during the current inflation of the cuff 14 may be measured. For example, the pressure in the cuff 14 can be measured and converted into the digital domain by an analogue-to-digital converter to acquire a time series of pressure data and numerical differentiation methods can be applied to determine the pressure in the cuff 14 over time dP/dt. The volume of fluid flow into the cuff during the current inflation of the cuff 14 may also be measured. It may be assumed that the internal volume of the cuff 14 is negligible at the start of the inflation or the internal volume of the cuff 14 at the start of the current inflation of the cuff 14 may be determined. For example, the internal volume of the cuff 14 at the start of the current inflation of the cuff 14 may be determined by integration of the volume of fluid flow into the cuff.

In some embodiments (e.g. when the current inflation of the cuff 14 is slow), the quasi-static cuff compliance $C_{QS}$ may be calculated using the following equation:

$$C_{QS} = \frac{\dot{P}_c}{\dot{V}_c}, \tag{3}$$

where $\dot{P}_c$ is the time derivative of the pressure in the cuff 14 and $\dot{V}_c$ is the time derivative of the volume of fluid flow into the cuff.

In some embodiments, when the volume of the cuff 14 $V_c$ and the pressure in the cuff 14 $P_c$ are known (e.g. from pressure measurements and an integration of fluid flow measurements, as described above), the quasi-static cuff compliance $C_{QS}$ at pressure Pc can be estimated from the known cuff volume-pressure relation using the following equation:

$$C_{QS}(P_C) = \left(\frac{\partial V_c}{\partial P_c}\right)_{P_C} + C_C. \tag{4}$$

Although examples have been provided for the way in which the cuff compliance may be determined, a person skilled in the art will be aware of other ways in which the cuff compliance can be determined. Moreover, although examples have been provided for the way in which the apparatus 12 may be configured to estimate the size of the cuff 14, a person skilled in the art will be aware of other ways in which the apparatus 12 may be configured to estimate the size of the cuff 14 and any combination of ways in which the apparatus 12 may be configured to estimate the size of the cuff 14 are possible.

Thus, at block 202 of FIG. 2, the size of the cuff 14 (or cuff size) is estimated Generally, subjects with a certain size of limb are eligible for certain cuff sizes. As such, the cuff size can be indicative of a size of a limb of the subject 18 around which the cuff 14 is worn. The size of the limb of the subject 18 around which the cuff 14 is worn may, for example, be a circumference or a circumference range (e.g. a range from a minimum circumference to a maximum circumference) of the limb of the subject 18 around which the cuff 14 is worn. An example of possible circumference ranges of a limb (e.g. an arm) for different cuff sizes is provided in the following table:

| Cuff size | Minimum circumference [cm] | Maximum circumference [cm] |
| --- | --- | --- |
| A | 10 | 15 |
| B | 14 | 21.5 |
| C | 20.5 | 28 |
| D | 27 | 35 |
| E | 34 | 43 |
| F | 42 | 54 |

The size of the limb of the subject 18 around which the cuff 14 is worn can be indicative of a feature (e.g. a biometric feature) of the subject 18 that distinguishes the subject 18 from other subjects or that can be used to classify the subject 18 into one or more categories of subject. For example, in some embodiments, the feature of the subject 18 may be any one or more of a physical feature of the subject 18 and a demographic feature of the subject 18. Examples of a physical feature of the subject 18 include, but are not limited to, a height (or a height range) of the subject 18, or any other physical feature of the subject 18, or any combination of physical features of the subject 18. Examples of a demographic feature of the subject 18 include, but are not limited to, an age (or an age range) of the subject 18, a gender (or a gender range) of the subject 18, or any other demographic feature of the subject 18, or any combination of demographic features of the subject 18. The size of the limb (e.g. the circumference of an arm) of the subject 18 may be assumed to directly correlate to the height of the subject 18 according to some embodiments, e.g. a relatively high arm circumference for a given age of subject can be related to a relatively high height for that given age of subject.

Thus, at block 202 of FIG. 2, a size of the cuff 14 is estimated during a current inflation of the cuff 14. Then, at block 204 of FIG. 2, the estimated size of the cuff 14 is compared to a previous size of the cuff 14 estimated during an inflation of the cuff 14 that immediately preceded the current inflation of the cuff 14. At block 206 of FIG. 2, if the estimated size of the cuff 14 differs from the previous size of the cuff 14 by more than a predefined amount, a pressure up to which the cuff 14 is inflated before deflation of the cuff 14 starts is changed. As mentioned earlier, the pressure up to which the cuff 14 is inflated before deflation of the cuff 14 starts may be referred to as "the starting pressure for deflation". Thus, at block 206 of FIG. 2, the starting pressure for deflation is changed. In some embodiments, where the estimated size of the cuff 14 differs from the previous size of the cuff 14 by more than the predefined amount, the estimated size in the cuff 14 may be referred to as being significantly different from the previous size of the cuff 14.

In some embodiments, if the immediately preceding starting pressure for deflation is reached before completion of the cuff size estimation and comparison, inflation of the cuff 14 may be paused at the immediately preceding starting pressure for deflation while the cuff size estimation and comparison is completed. As previously mentioned, the immediately preceding starting pressure for deflation is the pressure up to which the cuff 14 was inflated during the inflation that immediately preceded the current inflation. If the estimated size of the cuff 14 differs from the previous size of the cuff 14 by more than the predefined amount, the pressure up to which the cuff 14 is inflated before deflation of the cuff 14 starts (i.e. the starting pressure for deflation) can then be changed upon completion of the cuff size estimation and comparison according to these embodiments.

In some embodiments, if upon completion of the cuff size estimation and comparison, the pressure to which the starting pressure for deflation is to change is determined to be less than or equal to a current pressure, the starting pressure for deflation can instead be changed to the current pressure. Thus, in these embodiments, inflation of the cuff 14 is stopped and deflation of the cuff 14 starts at the current pressure.

In some embodiments, the apparatus 12 can be configured to change the pressure up to which the cuff 14 is inflated before deflation of the cuff 14 starts (i.e. the starting pressure for deflation) based on the estimated size of the cuff 14. Thus, according to some embodiments, an appropriate pressure up to which the cuff 14 is to be inflated before deflation of the cuff 14 starts (i.e. an appropriate starting pressure for deflation) can be inferred from the estimated size of the cuff 14. For example, in some embodiments, the apparatus 12 can be configured to change the pressure up to which the cuff 14 is inflated before deflation of the cuff 14 starts (i.e. the starting pressure for deflation) based on the estimated size of the cuff 14 by being configured to determine an expected blood pressure range (or an expected blood pressure value) for the subject 18 based on the estimated size of the cuff 14 and change the pressure up to which the cuff 14 is inflated before deflation of the cuff 14 starts (i.e. the starting pressure for deflation) based on the determined expected blood pressure range for the subject 18. In some embodiments, the expected blood pressure range (or value) can comprise an expected systolic blood pressure range (or value), e.g. an expected maximum systolic blood pressure range (or value).

In some embodiments, the apparatus 12 may be configured to determine the expected blood pressure range (or value) for the subject 18 based on the estimated size of the cuff 14 by being configured to compare the estimated size of the cuff 14 to a plurality of reference sizes of the cuff 14, each stored with a corresponding reference blood pressure range (or value), and determine the expected blood pressure range for the subject 18 as the reference blood pressure range (or value) that is stored with the reference size of the cuff 14 that is the same as or differs the least from the estimated size of the cuff 14. In some embodiments, the plurality of reference sizes of the cuff 14 and corresponding reference blood pressure ranges (or values) may be stored in the form of a look-up table. In some embodiments, the plurality of reference sizes of the cuff 14 and corresponding reference blood pressure ranges (or values) may be based on data acquired from a population. Thus, in some embodiments, the apparatus 12 may be configured to determine the expected blood pressure range (or value) for the subject 18 based on the estimated size of the cuff 14 and population data.

As mentioned earlier, the estimated size of the cuff 14 can be indicative of the size of the limb of the subject 18 around which the cuff 14 is worn and the size of the limb of the subject 18 around which the cuff 14 is worn can be indicative of a feature (e.g. a biometric feature) of the subject 18 that distinguishes the subject 18 from other subjects or that can be used to classify the subject 18 into one or more categories of subject. Thus, in other embodiments, the apparatus 12 may be configured to determine the expected blood pressure range (or value) for the subject 18 based on the estimated size of the cuff 14 by being configured to determine, based on the estimated size of the cuff 14, a feature (e.g. a biometric feature) of the subject 18 that distinguishes the subject 18 from other subjects or that can be used to classify the subject 18 into one or more categories of subject and then to determine the expected blood pressure range (or value) for the subject 18 based on the determined feature of the subject 18. For example, it is generally known that pediatric subjects (e.g. infants, children, and adolescents) have lower blood pressures, or lower blood pressure ranges, than adult subjects.

In some embodiments, the apparatus 12 may be configured to determine the expected blood pressure range (or value) for the subject 18 based on the determined feature of the subject 18 by being configured to compare the determined feature of the subject 18 to a plurality of reference features, each stored with a corresponding reference blood pressure range (or value), and determine the expected blood pressure range for the subject 18 as the reference blood pressure range (or value) that is stored with the reference feature that is the same as or differs the least from the determined feature of the subject 18. In some embodiments, the plurality of reference features and corresponding reference blood pressure ranges (or values) may be stored in the form of a look-up table. In some embodiments, the plurality of reference features and corresponding reference blood pressure ranges (or values) may be based on data acquired from a population. Thus, in some embodiments, the apparatus 12 may be configured to determine the expected blood pressure range (or value) for the subject 18 based on the determined feature and population data.

The population data (e.g. the plurality of reference features and corresponding reference blood pressure ranges or values) may be stored locally, such as in a memory of the apparatus 12, and/or in a memory that is external to (e.g. separate to or remote from) the apparatus 12, such as a general patient database (e.g. located on a server, such as a server next to a nursing post). Thus, the apparatus 12 (or the controller of the apparatus 12) can be configured to acquire population data from one or more memories according to some embodiments. The apparatus 12 (or the controller of the apparatus 12) can communicate with and/or connect to (e.g. be coupled to) one or more memories in any suitable way, e.g. via the communications interface described earlier. The population data stored in one or more memories may be updated on a regular basis (e.g. as a software feature). In some embodiments, the apparatus 12 (or the controller of the apparatus 12) may select one or more memories from which to acquire population data. For example, in some embodiments, the apparatus 12 (or the controller of the apparatus 12) may select one or more memories with the most up-to-date population data. In some embodiments, while population data stored in memory is being updated, the apparatus 12 (or the controller of the apparatus 12) may acquire population data from another memory. The population data may be stored in the form of a look-up table according to some embodiments.

In some embodiments, the starting pressure for deflation may be a pressure in a range from 80 to 180 mmHg, for example a pressure in a range from 85 to 175 mmHg, for example a pressure in a range from 90 to 170 mmHg, for example a pressure in a range from 100 to 165 mmHg, for example a pressure in a range from 105 to 160 mmHg, for example a pressure in a range from 110 to 155 mmHg, for example a pressure in a range from 115 to 150 mmHg, for example a pressure in a range from 120 to 145 mmHg, for example a pressure in a range from 125 to 140 mmHg, for example a pressure in a range from 130 to 135 mmHg. For example, the starting pressure for deflation may be a pressure selected from 80 mmHg, 85 mmHg, 90 mmHg, 95 mmHg, 100 mmHg, 105 mmHg, 110 mmHg, 115 mmHg, 120 mmHg, 125 mmHg, 130 mmHg, 135 mmHg, 140 mmHg, 145 mmHg, 150 mmHg, 155 mmHg, 160 mmHg, 165 mmHg, 170 mmHg, 175 mmHg, 180 mmHg, or any integer or non-integer value between these example pressures.

In some embodiments, the starting pressure for deflation may be a pressure of at least 80 mmHg, for example at least 85 mmHg, for example at least 90 mmHg, for example at least 95 mmHg, for example at least 100 mmHg, for example at least 105 mmHg, for example at least 110 mmHg, for example at least 115 mmHg, for example at least 120 mmHg, for example at least 125 mmHg, for example at least 130 mmHg, for example at least 135 mmHg, for example at least 140 mmHg, for example at least 145 mmHg, for example at least 150 mmHg, for example at least 155 mmHg, for example at least 160 mmHg, for example at least 165 mmHg, for example at least 170 mmHg, for example at least 175 mmHg, for example 180 mmHg.

In some embodiments, the starting pressure for deflation may be a pressure that is equal to (or approximately equal to) an expected blood pressure or, more specifically systolic blood pressure, for the subject. For all subjects (e.g. excluding neonatal subjects), the expected blood pressure (or systolic blood pressure) for the subject may be at least 100 mmHg according to some embodiments. For example, in some embodiments, the expected blood pressure (or systolic blood pressure) for a pediatric subject (e.g. excluding neonatal subjects) may be in a range from 100 to 120 mmHg (e.g. 110 mmHg). Similarly, for example, in some embodiments, the expected blood pressure (or systolic blood pressure) for an adult subject may be in a range from 120 to 180 mmHg (e.g. 150 mmHg). In some embodiments, the expected blood pressure (or systolic blood pressure) for a neonatal subject may be in a range from 70 to 100 mmHg (e.g. 85 mmHg). The expected blood pressure (or systolic blood pressure) for a neonatal subject can depend on age and/or gestational age, e.g. the youngest and/or smallest neonatal subjects may have an expected blood pressure (or systolic blood pressure) of approximately 70 mmHg and the oldest and/or largest neonatal subjects may have an expected blood pressure (or systolic blood pressure) of approximately 100 mmHg according to some embodiments.

In an example embodiment, the estimated size of the cuff 14 indicates that the subject 18 has an arm circumference of up to 15 cm (which is the size of the limb of the subject 18) and an arm circumference of up to 15 cm is indicative of the subject 18 being aged up to 4.5 years (which may be extracted from population data stored in a memory). Thus, based on the estimated size of the cuff 14 in this example, the apparatus 12 determines a feature of the subject 18, which is that the subject 18 is aged up to 4.5 years. By comparing the determined feature to a plurality of reference features, each stored in a memory with a corresponding reference blood pressure value in this example, the apparatus 12 determines (or extracts) from the memory that the blood pressure that corresponds to boys aged 4 is 110 mmHg and girls aged 4 is 107 mmHg. Thus, in this example, the apparatus 12 may determine (from population data stored in the memory) that the expected blood pressure value for the subject 18 is (most likely) equal to or less than (i.e. not higher than) 100 mmHg. Thus, if the estimated size of the cuff 14 differs from the previous size of the cuff 14 by more than a predefined amount in this example, the apparatus 12 can change the pressure up to which the cuff 14 is inflated before deflation of the cuff 14 starts to a value in a range from 90 mmHg to 110 mmHg. In some embodiments, the pressure up to which the cuff 14 is inflated before deflation of the cuff 14 starts may be set to a value equal to or approximately equal to (e.g. slightly higher than) an expected systolic blood pressure. Thus, for a child cuff like in the example, the pressure up to which the cuff 14 is inflated before deflation of the cuff 14 starts may be set to, e.g. 100 or 110 mmHg.

In another example of such an embodiment, the estimated size of the cuff 14 indicates that the subject 18 has an arm circumference of at least 28 cm (which is the size of the limb of subject 18) and an arm circumference of at least 28 cm is indicative of the subject 18 being an adult subject. Thus, based on the estimated size of the cuff 14 in this example, the apparatus 12 determines a feature of the subject 18, which is that the subject 18 is an adult subject. By comparing the determined feature to a plurality of reference features, each stored in a memory with a corresponding reference blood pressure value in this example, the apparatus 12 determines (or extracts) from the memory that the blood pressure that corresponds to adults is a blood pressure in a range from 120 to 180 mmHg (e.g. a blood pressure of 150 mmHg).

An example look-up table that maps a size of a cuff 14 to a default starting pressure (i.e. a pressure up to which the cuff 14 is to be inflated before deflation of the cuff 14 starts) is shown below:

| Cuff size | Minimum circumference [cm] | Maximum circumference [cm] | Default starting pressure [mmHg] |
| --- | --- | --- | --- |
| A | 10 | 15 | 100 (90-110) |
| B | 14 | 21.5 | 120 (100-130) |
| C | 20.5 | 28 | 150 (120-180) |
| D | 27 | 35 | 150 (120-180) |
| E | 34 | 43 | 150 (120-180) |
| F | 42 | 54 | 150 (120-180) |

Thus, in general, one or more memories may store (e.g. in a look-up table) a plurality of default starting pressures (i.e. a plurality of pressures up to which the cuff 14 is to be inflated before deflation of the cuff 14 starts) and a size of the cuff 14 corresponding to each of the plurality of default starting pressures. In this way, once the size of the cuff 14 is estimated, the apparatus 12 (or a controller of the apparatus 12) can determine (or extract) from the one or more memories a corresponding default starting pressure for that size of cuff 14. In some embodiments, the plurality of stored default starting pressures can comprise a minimum default starting pressure (i.e. a minimum pressure up to which the cuff 14 is to be inflated before deflation of the cuff 14 starts) $p_{min}$ and a maximum default starting pressure (i.e. a maximum pressure up to which the cuff 14 is to be inflated before deflation of the cuff 14 starts) $p_{max}$. Thus, in these embodiments, the minimum default starting pressure $p_{min}$ and the maximum default starting pressure $p_{max}$ can be stored with the size of the cuff 14 corresponding to each of the minimum default starting pressure $p_{min}$ and the maximum default starting pressure $p_{max}$. The minimum default starting pressure $p_{min}$ can be for the smallest cuff (e.g. for a cuff 14 for a pediatric subject, such as an infant, a child or an adolescent) and the maximum default starting pressure $p_{max}$ can be for the largest cuff (e.g. for a cuff 14 for an adult).

The values of the plurality of default starting pressures stored in the one or more memories depend on the blood pressure (or, more specifically, the systolic blood pressure) distribution over a population (as a function of a volume of the cuff 14). The values of the plurality of default starting pressures stored in the one or more memories can be selected such that the values are (e.g. slightly) larger than a blood pressure (or, more specifically, a systolic blood pressure) of a majority of the population, e.g. 90% of the population. As an example, a minimum default starting pressure $p_{min}$ for the smallest cuff (e.g. for a cuff 14 for a pediatric subject, such as an infant, a child or an adolescent) may be selected to be 100 mmHg (or a value in a range from 80 to 110 mmHg). Similarly, as an example, a maximum default starting pressure $p_{max}$ for the largest cuff (e.g. for a cuff 14 for an adult) may be selected to be 150 mmHg (or a value in a range from 120 to 180 mmHg).

In some embodiments, the one or more memories may also store (e.g. in the look-up table) one or more characteristics of the cuff 14 during the current inflation of the cuff 14 corresponding to each of the plurality of default starting pressures. The one or more characteristics of the cuff 14 during the current inflation of the cuff 14 can comprise any one or more of the characteristics mentioned earlier, such as the time taken for the cuff 14 to be inflated from the baseline pressure up to the predefined pressure, the speed (e.g. average speed) at which the cuff 14 inflates, the internal volume of the cuff 14, the volume of fluid into the cuff 14 and the maximum pressure up to which the cuff 14 is inflated, the measure of the compliance of the cuff 14, and/or any other characteristics of the cuff 14 during the current inflation of the cuff 14.

The manner in which the apparatus 12 is configured where the estimated size of the cuff 14 differs from the previous size of the cuff 14 by more than a predefined amount has thus been described with reference to FIG. 2. On the other hand, in some embodiments (not illustrated in FIG. 2), the apparatus 12 may be configured to, if the estimated size of the cuff 14 differs from the previous size of the cuff 14 by less than the predefined amount or if the estimated size of the cuff 14 is the same as the previous size of the cuff 14, determine the pressure up to which the cuff 14 is inflated before deflation of the cuff 14 starts based on a blood pressure value (e.g. a systolic blood pressure value) determined during a deflation of the cuff 14 that immediately preceded the current inflation of the cuff 14. Where the estimated size of the cuff 14 differs from the previous size of the cuff 14 by less than the predefined amount or the estimated size of the cuff 14 is the same as the previous size of the cuff 14, the estimated size in the cuff 14 may be referred to as being similar to the previous size of the cuff 14.

In some embodiments, the predefined amount that is referred to herein may be at least 10%, for example at least 15%, for example at least 20%, for example at least 25%, for example at least 30%, for example at least 35%, for example 40%, for example at least 45%, for example at least 50%. In some embodiments, the predefined amount referred to herein may be an amount in a range from 10% to 50%, for example in a range from 15% to 45%, for example in a range from 20% to 40%, for example in a range from 25% to 35%. For example, the predefined amount referred to herein may be an amount selected from 10%, 15%, 20%, 25%, 30%, 35%, 40%, 45%, 50%, or any non-integer amount between the mentioned values, or any other amount that is in a range from 10% to 50%. Although some examples have been provided for the predefined amount referred to herein, it will be understood that the predefined amount referred to herein may be any amount that is at least 10% or that is in the range from 10% to 50%.

Although not illustrated in FIG. 2, in some embodiments, the apparatus 12 may be configured to acquire a signal indicative of pressure oscillations detected in the cuff 14 during deflation of the cuff 14. In some of these embodiments, the apparatus 12 (or the controller of the apparatus 12) can also be configured to determine (or measure) a blood pressure value for the subject 18 based on the acquired signal. Alternatively, a module external to (e.g. separate to or remote from) the apparatus 12 may be configured to acquire a signal indicative of pressure oscillations detected in the cuff 14 during deflation of the cuff 14 and determine (or measure) a blood pressure value for the subject 18 based on the acquired signal. Thus, the apparatus 12 (or an external module) can be configured to determine a blood pressure value for the subject 18 during deflation of the cuff 14 according to some embodiments.

In some embodiments, the signal indicative of pressure oscillations detected in the cuff 14 during deflation of the cuff 14 may be acquired (or measured) gradually or in a step-wise manner. For example, in some step-wise embodiments, the signal indicative of pressure oscillations detected in the cuff 14 during deflation of the cuff 14 may be acquired (or measured) at plateau pressures and the pressure in the cuff 14 may be reduced in step-wise fashion between the plateau pressures. A plateau pressure can be defined as a constant pressure level at which the signal indicative of pressure oscillations is measured, e.g. as part of a blood pressure measurement.

As the blood pressure value for the subject 18 can be determined based on a signal acquired during deflation (or at the deflation stage) of the cuff 14, the apparatus 12 is for use in deflation-based blood pressure measurements. Also, the technique is non-invasive. Thus, more specifically, the apparatus 12 is for use in deflation-based non-invasive blood pressure (NIBP) measurements. In some embodiments, the acquired signal may be in a frequency range that corresponds to a heart rate range, e.g. of 30 beats/min to 300 beats/min. For example, the acquired signal may be in a frequency range from 0.5 Hz to 5 Hz according to some embodiments.

In any of the embodiments described herein, at least one or all of the steps that the apparatus 12 is configured to perform can be automated.

There is also provided a computer program product comprising a computer readable medium. The computer readable medium has computer readable code embodied therein. The computer readable code is configured such that, on execution by a suitable computer or processor, the computer or processor is caused to perform the method described herein. The computer readable medium may be, for example, any entity or device capable of carrying the computer program product. For example, the computer readable medium may include a data storage, such as a ROM (such as a CD-ROM or a semiconductor ROM) or a magnetic recording medium (such as a hard disk). Furthermore, the computer readable medium may be a transmissible carrier, such as an electric or optical signal, which may be conveyed via electric or optical cable or by radio or other means. When the computer program product is embodied in such a signal, the computer readable medium may be constituted by such a cable or other device or means. Alternatively, the computer readable medium may be an integrated circuit in which the computer program product is embedded, the integrated circuit being adapted to perform, or used in the performance of, the method described herein.

There is thus provided herein an apparatus, a method and a computer program product that address the limitations associated with the existing techniques.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for use with a wearable cuff in measuring blood pressure, wherein the cuff is inflatable to pressurize a measurement site of a subject and the apparatus is configured to:
   estimate a size of the cuff during a current inflation of the cuff;
   compare the estimated size of the cuff to a previous size of the cuff estimated during an inflation of the cuff that immediately preceded the current inflation of the cuff; and
   when the estimated size of the cuff differs from the previous size of the cuff by more than a predefined amount, change a pressure up to which the cuff is inflated before deflation of the cuff starts.

2. The apparatus as claimed in claim 1, wherein the apparatus is configured to change the pressure up to which the cuff is inflated before deflation of the cuff starts based on the estimated size of the cuff.

3. The apparatus as claimed in claim 2, wherein the apparatus is configured to change the pressure up to which the cuff is inflated before deflation of the cuff starts based on the estimated size of the cuff by being configured to:
   determine an expected blood pressure range for the subject based on the estimated size of the cuff; and
   change the pressure up to which the cuff is inflated before deflation of the cuff starts based on the determined expected blood pressure range for the subject.

4. The apparatus as claimed in claim 3, wherein the apparatus is configured to determine the expected blood pressure range for the subject based on the estimated size of the cuff by being configured to:
   compare the estimated size of the cuff to a plurality of reference sizes of the cuff, each stored with a corresponding reference blood pressure range; and
   determine the expected blood pressure range for the subject as the reference blood pressure range that is stored with the reference size of the cuff that is the same as or differs the least from the estimated size of the cuff.

5. The apparatus as claimed in claim 4, wherein the plurality of reference sizes of the cuff and corresponding reference blood pressure ranges are based on data acquired from a population.

6. The apparatus as claimed in claim 1, wherein the apparatus is configured to:
   when the estimated size of the cuff differs from the previous size of the cuff by less than the predefined amount or when the estimated size of the cuff is the same as the previous size of the cuff, determine the pressure up to which the cuff is inflated before deflation of the cuff starts based on a blood pressure value determined during a deflation of the cuff that immediately preceded the current inflation of the cuff.

7. The apparatus as claimed in claim 1, wherein the apparatus is configured to estimate the size of the cuff during the current inflation of the cuff based on a time taken for the cuff to be inflated from a baseline pressure up to a predefined pressure.

8. The apparatus as claimed in claim 1, wherein the apparatus is configured to estimate the size of the cuff during the current inflation of the cuff based on an average speed at which the cuff inflates.

9. The apparatus as claimed in claim 8, wherein the apparatus is configured to:
determine the average speed at which the cuff inflates as the average speed at which the cuff inflates once a predefined time period after a start of the current inflation of the cuff has passed.

10. The apparatus as claimed in claim 1, wherein the apparatus is configured to estimate the size of the cuff during the current inflation of the cuff based on an internal volume of the cuff.

11. The apparatus as claimed in claim 1, wherein the apparatus is configured to estimate the size of the cuff during the current inflation of the cuff based on a volume of fluid into the cuff and a maximum pressure up to which the cuff is inflated.

12. The apparatus as claimed in claim 1, wherein the apparatus is configured to estimate the size of the cuff during the current inflation of the cuff based on a measure of a compliance of the cuff.

13. A system for use in measuring blood pressure, the system comprising:
the apparatus as claimed in claim 1; and
the cuff that is inflatable to pressurize the measurement site of the subject.

14. A method of operating an apparatus for use with a wearable cuff in measuring blood pressure, wherein the cuff is inflatable to pressurize a measurement site of a subject, the method comprising:
estimating a size of the cuff during a current inflation of the cuff;
comparing the estimated size of the cuff to a previous size of the cuff estimated during an inflation of the cuff that immediately preceded the current inflation of the cuff; and
based on the estimated size of the cuff differing from the previous size of the cuff by more than a predefined amount, changing a pressure up to which the cuff is inflated before deflation of the cuff starts.

15. In an apparatus for use with a wearable cuff in measuring blood pressure, a computer program product comprising a non-transitory computer readable medium, the non-transitory computer readable medium having computer readable code stored therein, the computer readable code being configured such that, when executed by a computer or a processor, the computer readable code causes the computer or processor to:
estimate a size of the cuff during a current inflation of the cuff;
compare the estimated size of the cuff to a previous size of the cuff estimated during an inflation of the cuff that immediately preceded the current inflation of the cuff; and
when the estimated size of the cuff differs from the previous size of the cuff by more than a predefined amount, change a pressure up to which the cuff is inflated before deflation of the cuff starts.

16. The computer program product as claimed in claim 15, wherein the computer readable code further causes the computer or processor to change the pressure up to which the cuff is inflated before deflation of the cuff starts based on the estimated size of the cuff.

17. The computer program product as claimed in claim 16, wherein the computer readable code further causes the computer or processor to change the pressure up to which the cuff is inflated before deflation of the cuff starts based on the estimated size of the cuff by:
determining an expected blood pressure range for a subject based on the estimated size of the cuff; and
changing the pressure up to which the cuff is inflated before deflation of the cuff starts based on the determined expected blood pressure range for the subject.

18. The computer program product as claimed in claim 17, wherein the computer readable code further causes the computer or processor to determine the expected blood pressure range for the subject based on the estimated size of the cuff by:
comparing the estimated size of the cuff to a plurality of reference sizes of the cuff, each stored with a corresponding reference blood pressure range; and
determining the expected blood pressure range for the subject as the reference blood pressure range that is stored with the reference size of the cuff that is the same as or differs the least from the estimated size of the cuff.

19. The computer program product as claimed in claim 18, wherein the plurality of reference sizes of the cuff and corresponding reference blood pressure ranges are based on data acquired from a population.

20. The computer program product as claimed in claim 16, wherein the computer readable code further causes the computer or processor to:
when the estimated size of the cuff differs from the previous size of the cuff by less than the predefined amount or when the estimated size of the cuff is the same as the previous size of the cuff, determine the pressure up to which the cuff is inflated before deflation of the cuff starts based on a blood pressure value determined during a deflation of the cuff that immediately preceded the current inflation of the cuff.

* * * * *